(12) United States Patent
Fowler et al.

(10) Patent No.: US 8,946,122 B2
(45) Date of Patent: Feb. 3, 2015

(54) PESTICIDAL COMBINATIONS

(75) Inventors: Jeffrey David Fowler, Greensboro, NC (US); Colin Douglas Miln, Greensboro, NC (US)

(73) Assignee: Syngenta Crop Protection LLC, Greensboro, NC (US)

( * ) Notice: Subject to any disclaimer, the term of this patent is extended or adjusted under 35 U.S.C. 154(b) by 238 days.

(21) Appl. No.: 13/143,850

(22) PCT Filed: Jan. 7, 2010

(86) PCT No.: PCT/US2010/020344
§ 371 (c)(1),
(2), (4) Date: Nov. 11, 2011

(87) PCT Pub. No.: WO2010/080891
PCT Pub. Date: Jul. 15, 2010

(65) Prior Publication Data
US 2012/0045497 A1    Feb. 23, 2012

Related U.S. Application Data

(60) Provisional application No. 61/143,494, filed on Jan. 9, 2009.

(51) Int. Cl.
*A01N 25/00* (2006.01)
*A01N 59/00* (2006.01)
*A01N 25/04* (2006.01)
*A01N 25/08* (2006.01)

(52) U.S. Cl.
CPC ............... *A01N 25/04* (2013.01); *A01N 25/08* (2013.01)
USPC .......................................... 504/124; 424/405

(58) Field of Classification Search
USPC .......................................... 504/124; 424/405
See application file for complete search history.

(56) References Cited

U.S. PATENT DOCUMENTS

| 6,548,448 B2 | 4/2003 | Kostansek |
| 6,936,572 B2 * | 8/2005 | Stewart et al. ................ 504/362 |
| 6,955,823 B2 | 10/2005 | Casson et al. |

FOREIGN PATENT DOCUMENTS

| EP | 1922927 | 5/2008 |
| KR | 797072 | * 1/2008 |

OTHER PUBLICATIONS

RD 443013—Stable Emulsion—annonymous—Mar. 2001.*

* cited by examiner

*Primary Examiner* — Gina Justice
(74) *Attorney, Agent, or Firm* — James Cueva

(57) ABSTRACT

Stabilized liquid agrochemical compositions are provided which comprise flowable non-aqueous dispersion concentrates comprising a continuous substantially water-miscible liquid phase, a dispersed water-immiscible liquid phase, and a colloidal solid. In one embodiment, the dispersed phase comprises at least one water-sensitive agrochemically active ingredient and the colloidal solid is disposed at the interface between the dispersed phase and the continuous phase. In another embodiment, the water-sensitive agrochemically active ingredient is a solid but is dissolved in an oily liquid present in the dispersed phase, or is a solid and is dispersed within the dispersed phase, or is a solid complex of an agrochemical with a molecular complexing agent and is dispersed within the dispersed phase. The compositions of the invention can be used directly or with dilution to combat pests or as plant growth regulators.

22 Claims, No Drawings

PESTICIDAL COMBINATIONS

This application is a 371 of International Application No. PCT/US2010/020344 filed Jan. 7, 2010, which claims priority to U.S. 61/143,494 filed Sep. 9, 2009, the contents of which are incorporated herein by reference.

The present invention relates to stabilized, liquid, agrochemical compositions, the preparation of such compositions and a method of using such compositions to combat pests or as plant growth regulators.

BACKGROUND OF THE INVENTION

Agriculturally active ingredients are often provided in the form of concentrates suitable for dilution with water. Many forms of agricultural concentrates are known and these consist of the active ingredient and a carrier, which can include various components. Water-based concentrates are obtained by dissolving, emulsifying and/or suspending agriculturally active technical materials in water. Due to the relatively complex supply chain for crop protection agents, such concentrate formulations can be stored for long periods and may be subjected during storage and shipping to extreme temperature variations, high-shear and repetitive vibration patterns. Such supply chain conditions can increase the likelihood of formulation failure due to, for example, water mediated degradation and stability problems.

Accordingly, the efficient use of aqueous systems with certain agrochemicals and crop protection agents is restricted due to their poor chemical stability when exposed to water during storage. Typically, hydrolysis is the most common water-mediated degradation mechanism; however, agricultural concentrates with water-sensitive active ingredients are also subject to oxidation, dehalogenation, bond cleavage, Beckmann rearrangement and other forms of degradation on exposure to water.

In some cases it may be desirable to combine different agrochemicals to provide a single formulation taking advantage of the additive properties of each separate agrochemical and optionally an adjuvant or combination of adjuvants that provide optimum biological performance. For example, transportation and storage costs can be minimized by using a formulation in which the concentration of the active agrochemical(s) is as high as is practicable and in which any desired adjuvants are "built-in" to the formulation as opposed to being separately tank-mixed. The higher the concentration of the active agrochemical(s) however, the greater is the probability that the stability of the formulation may be disturbed, or that one or more components may phase separate.

Another challenge arises where a user of an agrochemical liquid concentrate formulation dilutes the formulation in water (for example in a spray tank) to form a dilute aqueous spray composition. Such agrochemical spray compositions are widely used, but their performance sometimes can be limited by the tendency for certain agrochemicals to degrade in a spray tank on exposure to water. For example, agrochemical breakdown can increase with increasing alkalinity and water temperature, and with the length of time the spray composition is left in the tank.

In addition, it may be desirable to improve the effectiveness of the agrochemicals by controlling the release rate of agrochemical into the application site from the formulation. For agrochemicals that are to any significant extent soluble in water, this is a particular challenge if water is present in the formulation, because of the tendency of the agrochemical to come to thermodynamic equilibrium and partially dissolve within the formulation. To the extent that the agrochemical dissolves, this reduces the physical stability of the formulation and negates any controlled release properties.

In addition, spray tank mixes can contain a variety of chemicals and adjuvants that may interact and change the effectiveness of one or more of the agrochemicals included therein. Incompatibility, poor water quality and insufficient tank agitation can lead to reduced effectiveness of sprays, phytotoxicity and can affect equipment performance.

Considering the variety of conditions and special situations under which agrochemical liquid concentrate formulation are stored, shipped an used around the world, there remains a need for concentrate formulations of agrochemicals, including water sensitive agrochemicals, that provide stability benefits under at least some of those conditions and situations. There is a further need for such formulations having high loading that are stable when diluted with water under a wide range of field conditions.

SUMMARY OF THE INVENTION

Stabilized liquid agrochemical compositions are provided which comprise flowable, non-aqueous dispersion concentrates comprising a continuous substantially water-miscible liquid phase, a dispersed water-immiscible liquid phase, and a colloidal solid. In one embodiment, the dispersed phase comprises at least one water-sensitive agrochemically active ingredient and the colloidal solid is disposed at the interface between the dispersed phase and the continuous phase. In another embodiment, the water-sensitive agrochemically active ingredient is a solid but is dissolved in an oily liquid present in the dispersed phase, or is a solid and is dispersed within the dispersed phase, or is a solid complex of an agrochemical with a molecular complexing agent and is dispersed within the dispersed phase. The compositions of the invention can be used directly or with dilution to combat pests or as plant growth regulators.

In accordance with the invention, it has been found that dispersible concentrates of a first non-aqueous water-immiscible liquid in a second non-aqueous substantially water-miscible liquid can be prepared by using colloidal solids to stabilize the dispersed phase as in a Pickering-type emulsion. A water-sensitive agrochemically active ingredient can be entrapped, suspended or dissolved within the dispersed phase, and other active ingredients may optionally be dissolved or suspended within the continuous phase. The novel Pickering-type emulsions of the invention, stabilized by colloidal particles, are stable with relatively large droplets, giving a usefully long period of protection for water-sensitive agrochemicals that has practical utility in terms of storage, shipment and use, and also giving the ability to control the release rate of the agrochemical into the target site from the formulation.

The water-immiscible liquid can be chosen to be sufficiently hydrophobic such that, when the concentrate is diluted into water to form an aqueous spray solution, the droplets of water-immiscible liquid (oil) protect the water-sensitive agrochemically active ingredient from exposure to water for a period of time depending principally on the size of the emulsified liquid (oil) droplets. In an embodiment, the size of the emulsion droplets is thus dependent on nature of the agrochemically active ingredient and one skilled in the art will readily determine the optimum size within the scope of the current invention.

The present invention also includes a method for combating or controlling pests or regulating the growth of plants at a locus such as soil or foliage which comprises treating said locus with a dispersion concentrate according to the invention or dispersing a concentrate according to the present invention in water and treating said locus with the obtained diluted aqueous formulation.

DETAILED DESCRIPTION OF THE INVENTION

Accordingly, in one embodiment, the non-aqueous liquid dispersion concentrate compositions of the present invention comprise:
a) a continuous, substantially water-miscible, non-aqueous liquid phase, optionally comprising at least one agrochemically active ingredient;
b) a dispersed, water-immiscible, non-aqueous liquid phase comprising at least one substantially water-sensitive agrochemically active ingredient, which is a solid but is dissolved in an oily liquid present in the dispersed phase, is a solid and is dispersed within the dispersed phase or is a solid complex of an agrochemical with a molecular complexing agent and is dispersed within the dispersed phase; and
c) at least one colloidal solid disposed at the interface between the dispersed phase and the continuous phase.

The term "substantially water-miscible" means a non-aqueous liquid that forms a single phase when present in water at a concentration up to at least 50 wt %.

The non-aqueous liquids suitable for use in the continuous phase a) are those that are substantially water-miscible. They include, for example, propylene carbonate such as JEFFSOL® AG-1555 (Huntsman); a water-miscible glycol selected from ethylene glycol, diethylene glycol, triethylene glycol, propylene glycol, dipropylene glycol, tripropylene glycol, butylene glycol, hexylene glycol and polyethylene glycols having a molecular weight of up to about 800; an acetylated glycol such as di(propylene glycol) methyl ether acetate or propylene glycol diacetate; triethyl phosphate; ethyl lactate; gamma-butyrolactone; a water-miscible alcohol such as propanol or tetrahydrofurfuryl alcohol; N-methyl pyrrolidone; dimethyl lactamide; and mixtures thereof. In one embodiment, the non-aqueous, substantially water-miscible liquid used in the continuous phase a) is a solvent for at least one agrochemically active ingredient. In another embodiment, the non-aqueous, substantially water-miscible liquid used in the continuous phase a) is fully miscible with water in all proportions.

In one embodiment, the non-aqueous liquid used in the dispersed water-immiscible, liquid (oil) phase b) must be substantially immiscible with water and the affinity of the liquid for the water-sensitive agrochemically active ingredient dissolved or suspended in the dispersed phase must be such that substantially all of the water-sensitive agrochemically active ingredient is partitioned in the dispersed phase and substantially none is partitioned in the continuous phase. Those skilled in the art will readily be able to determine whether a particular water-immiscible liquid meets this second criterion for the water-sensitive agrochemically active ingredient in question by following any standard test procedure for determining the partition coefficient of a compound (in this case, the oil-soluble, oil-miscible or oil-dispersed water-sensitive agrochemically active ingredient) between the continuous phase and the discontinuous (dispersed) liquid phase. Accordingly, in one embodiment, the dispersed, water-immiscible, non-aqueous liquid phase b) is immiscible with the continuous phase a).

In another embodiment, water-insoluble polymers can be used to impart hydrophobicity to solid particles of certain hydrophilic water-sensitive agrochemically active ingredients that otherwise would not be substantially partitioned in the dispersed liquid phase and/or have a suitable partition coefficient. Examples of suitable water-insoluble polymers useful for this purpose include copolymers of an α-olefin and an N-vinylpyrrolidone such as, for example, alkylated vinylpyrrolidone copolymers such as the Agrimers (e.g., Agrimer® AL-22, based on 1-ethenylhexadecyl-2-pyrrolidinone) (International Specialty Products (ISP) Corporation), or copolymers of an α-olefin and ethylene glycol such as, for example Atlox 4914 of Croda Corp. For example, such polymers can be used to impart hydrophobicity to agrochemically active ingredients such as a cyclopropene molecular encapsulating agent complex.

In one embodiment of the invention, the dispersed water-immiscible liquid phase b) comprises a non-aqueous liquid with sufficient hydrophobicity so that when the concentrate is emulsified upon dilution with water, the droplets of such water-immiscible liquid continue to protect the water-sensitive agrochemical from exposure to water in the diluted aqueous spray formulation for a period well within the acceptable range for such dilutions that are to be used for agricultural spray applications. For example, in one embodiment, a major amount of a water-sensitive agrochemical can be protected from exposure to water for more than about 1 hour in an agitated spray tank.

In one embodiment, when the concentrate is diluted in water, some water-sensitive agrochemical slowly diffuses out of the droplets of water-immiscible liquid. The agrochemical release rate from the emulsified droplets in the spray tank can be adjusted by varying the size of the dispersed liquid emulsion droplets in the concentrate, the concentration of active ingredient in the dispersed phase, the pH of the spray tank dispersion, and the amount and nature of colloidal solid used to stabilize the emulsion droplets.

In one embodiment, the water-immiscible liquid droplets have a volume-weighted median diameter as measured by diffraction light scattering of about 200 microns or less; more suitably from about 20 to about 150 microns.

Examples of water-immiscible, non-aqueous liquids suitable for use in the dispersed water-immiscible liquid phase b) include: petroleum distillates, vegetable oils, silicone oils, methylated vegetable oils, refined paraffins, isoparaffinic hydrocarbons (such as ISOPAR V, for example), mineral oils, alkyl amides, alkyl acetates, or other liquids and solvents with a log P of 3 or above, and mixtures thereof. In one embodiment, the water-immiscible, non-aqueous liquid used in the dispersed phase b) has a log P of about 4 or above.

Solids, such as silicas and clays, have been taught in the literature for use as viscosity modifiers in agrochemical formulations to inhibit gravity-driven sedimentation or cream separation by forming a network or gel throughout the continuous phase, thereby increasing the low-shear viscosity, and slowing the movement of small particles, surfactant micelles or emulsion droplets. The colloidal solids of the present invention instead stabilize the droplets of the dispersed liquid phase by adsorbing to the liquid-liquid interface, thereby forming a barrier around the droplets so that contacting or neighbouring droplets are not able to coalesce, irrespective of whether or not the emulsion droplets have collected in a sediment or a cream layer. It is possible to distinguish the two different functions—rheological modification or emulsion stabilization, by a functional test such as described below. The effectiveness of the colloidal solid in stabilizing the emulsions depends on particle size, particle shape, particle concentration, particle wettability and the interactions between particles. The colloidal solids must be small enough so that they can coat the surfaces of the dispersed liquid droplets, and the liquid droplets must be sufficiently small for good dispersion stability against sedimentation when diluted for use and small enough to provide an even product distribution at the target site. The colloidal solid also must have sufficient affinity for both the liquids forming the dispersed and continuous phases so that they are able to adsorb to the liquid-liquid interface and thereby stabilize the emulsion. This wetting characteristic, particle shape and suitability for Pickering-type emulsion stabilization may be readily assessed in formulations of sufficiently low viscosity (below about 2000 centipoise) to be useful in most liquid products, by combining the two immiscible liquid phases and the colloidal solid, and providing sufficient mechanical agitation to form an emulsion. If the resulting emulsion exhibits no substantial droplet coalescence over a period of 2 or more hours, as determined by the appearance of a liquid layer containing only the liquid that was earlier present in the dispersed phase, then the colloidal solid has sufficient affinity for the liquid-liquid interface to stabilize the Pickering-type emulsion of the invention against coalescence.

In one embodiment, the colloidal solid also assists to preclude migration of the water-sensitive agrochemical from the dispersed phase into the continuous phase.

In some cases the spontaneity, and stability of the dispersed phase emulsion against flocculation on dilution with water, can be improved, by adding one or more emulsifiers to the continuous water-miscible non-aqueous solvent phase of the dispersion concentrate. Examples of suitable emulsifiers which serve in this manner include: phosphate esters of ethoxylated tristyrylphenol (such as Soprophor 3D33 of Rhodia), polyalkoxylated alcohols such as Rhodasurf BC-610 of Rhodia or polyalkoxylated (4 mole EO) sorbitan monooleate (Tween 21 of Croda).

In another embodiment, the physical stability, flowability and handling properties of the dispersion concentrate can be improved by adding one or more surfactants or dispersants to the continuous water-miscible non-aqueous solvent phase, including polyvinylpyrrolidone (Agrimer 90 of ISP), acetic acid ethenyl ester polymer with 1-ethenyl-2-pyrrolidone (Agrimer VA 5I of ISP), and nonionic surfactants. Preferred nonionic surfactants are those that are hydrophilic with an HLB above about 12, such as Atplus MBA 13/30 of Croda, amine based block copolymers such as Tertronic 1107 of BASF, or polyalkoxylated butanol (Toximul 8320 of Stepan).

In one embodiment, the colloidal solids have a number-weighted median particle size diameter as measured by scanning electron microscopy of 0.01-2.0 microns, particularly 0.5 microns or less, more particularly 0.1 microns or less.

A wide variety of solid materials may be used as colloidal stabilizers for the dispersions of the present invention including carbon black, metal oxides, metal hydroxides, metal carbonates, metal sulfates, polymers, silica and clays. Suitable colloidal stabilizers are insoluble in any of the liquid phases present in the concentrate formulation, and also substantially insoluble in any liquid used to dilute such formulation prior to application to the target site. If an agrochemically active ingredient has suitably low solubility in any liquid used to dilute the composition, and in both the continuous and dispersed liquid phases, that is below about 100 ppm at room temperature, and can be prepared at a suitable particle size, and has suitable wetting properties for the liquid-liquid interface as described above, then it is also possible that this active ingredient can serve as the colloidal stabilizer. Examples of particulate inorganic materials are oxy compounds of at least one of calcium, magnesium, aluminium and silicon (or derivatives of such materials), such as silica, silicate, marble, clays and talc. Particulate inorganic materials may be either naturally occurring or synthesised in reactors. The particulate inorganic material may be a mineral chosen from, but not limited to, kaolin, bentonite, alumina, limestone, bauxite, gypsum, magnesium carbonate, calcium carbonate (either ground or precipitated), perlite, dolomite, diatomite, huntite, magnesite, boehmite, sepiolite, palygorskite, mica, vermiculite, illite, hydrotalcite, hectorite, halloysite and gibbsite. Further suitable clays (for example aluminosilicates) include those comprising the kaolinite, montmorillonite or illite groups of clay mineral. Other specific examples are attapulgite, laponite and sepiolite.

In one aspect of the invention, the particulate inorganic material is kaolin clay. Kaolin clay is also referred to as china clay or hydrous kaolin, and contains predominantly mineral kaolinite ($Al_2Si_2O_5(OH)_4$), a hydrous aluminium silicate (or aluminosilicate).

Surface-modified means that the inorganic particle surface has been modified so as to have reactive groups. The surface of the particles may be modified using a wide variety of chemicals, with the general structure X—Y—Z, in which X is a chemical moiety with a high affinity for the particle surface; Z is a (reactive) chemical moiety with a desired functionality; and Y is a chemical moiety that links X and Z together.

X may be, for example, an alkoxy-silane group such as tri-ethoxysilane or tri-methoxysilane, which is particularly useful when the particles have silanol (SiOH) groups on their surface. X may also be, for example, an acid group (such as a carboxylic or an acrylic acid group) which is particularly useful when the particles have basic groups on their surface. X may also be, for example, a basic group (such as an amine group), an epoxy group, or an unsaturated group (such as an acrylic or vinyl group).

Y can be any chemical group that links X and Z together, for example a polyamide, a polyisocyanate, a polyester or an alkylene chain; more suitably it is an alkylene chain; and even more suitably it is a $C_{2-6}$ alkylene chain, such as ethylene or propylene.

Reactive groups Z can be selected from any groups, and may be different from Y, which can be used to react with a cross-linker.

In one embodiment of the present invention, the compositions optionally contain Ostwald ripening inhibitors. Ostwald ripening inhibitors suitable for use in the present invention are polymers soluble only in the dispersed water-immiscible oil phase, but not in the continuous water-miscible solvent phase. Polymeric materials suitable for use as the Ostwald ripening inhibitors in the practice of the invention include polymers or oligomers having a molecular weight of at least 200, in particular a molecular weight of at least 400. The chemical composition of the material can be selected based on its ability to be solubilized in the dispersed phase. Suitable materials may be homopolymers or co-polymers, for example those described in "Polymer Handbook" 3rd Edition edited by J. Brandrup and E. H. Immergut.

Examples of suitable homopolymers include polyolefins such as polyallene, polybutadiene, polyisoprene, and poly (substituted butadienes) such as poly(2-t-butyl-1,3-butadiene), poly(2-chlorobutadiene), poly(2-chloromethyl butadiene), polyphenylacetylene, polyethylene, chlorinated polyethylene, polypropylene, polybutene, polyisobutene, polybutylene oxides, or copolymers of polybutylene oxides with propylene oxide or ethylene oxide, polycyclopentylethylene, polycyclohexylethylene, polyacrylates including polyalkylacrylates and polyarylacrylates, polymethacrylates including polyalkylmethacrylates and polyarylmethacrylates, polydisubstituted esters such as poly(di-n-butylitaconate), and poly(amylfumarate), polyvinylethers such as poly(butoxyethylene) and poly(benzyloxyethylene), poly(methyl isopropenyl ketone), polyvinyl chloride, polyvinyl acetate, polyvinyl carboxylate esters such as polyvinyl propionate, polyvinyl butyrate, polyvinyl caprylate, polyvinyl laurate, polyvinyl stearate, polyvinyl benzoate, polystyrene, poly-t-butyl styrene, poly (substituted styrene), poly(biphenyl ethylene), poly(1,3-cyclohexadiene), polycyclopentadiene, polyoxypropylene, polyoxytetramethylene, polycarbonates such as poly(oxycarbonyloxyhexamethylene), polysiloxanes, in particular, polydimethyl cyclosiloxanes and organo-soluble substituted polydimethyl siloxanes such as alkyl, alkoxy, or ester substituted polydimethylsiloxanes, liquid polysulfides, natural rubber and hydrochlorinated rubber, ethyl-, butyl- and benzyl-celluloses, cellulose esters such as cellulose tributyrate, cellulose tricaprylate and cellulose tristearate and natural resins such as colophony, copal and shellac.

Examples of suitable co-polymers are co-polymers of styrene, alkyl styrenes, isoprene, butenes, butadiene, acrylonitrile, alkyl acrylates, alkyl methacrylates, vinyl chloride, vinylidene chloride, vinyl esters of lower carboxylic acids and alpha, beta-ethylenically unsaturated carboxylic acids and esters thereof, including co-polymers containing three or more different monomer species therein.

When used, the Ostwald ripening inhibitors may be employed in an amount of from 0.1 to 20%, in particular from 0.2 to 6% by weight of the dispersed phase. Mixtures of polymers may be employed.

The type and amount of colloidal solid is selected so as to provide acceptable physical stability of the composition. This can readily be determined by one of skill in the art by routine evaluation of a range of compositions having different amounts of this component. For example, the ability of the colloidal solids to stabilize the composition can be verified by preparing a test sample with the colloidal solid and it can be confirmed that the emulsion is stable and does not exhibit coalescence. Coalescence is apparent by the formation of large oil droplets visible to the eye, and ultimately by the formation of a layer of oil within the formulation. Physical stability of the composition is acceptable if no significant coalescence is evident following storage for at least 7 to 30 days over the range of temperatures from 0° C. to about 50° C. Stable compositions within the scope of the present invention also include those compositions that can easily be resuspended or redispersed with only a minor amount of agitation—in such cases the formulation is exhibiting creaming or sedimentation, as described by T. F. Tadros (Surfactants in Agrochemicals, Marcel Dekker, New York (1995)).

In some cases the performance of the colloidal solid in stabilizing the formulation may be enhanced by manipulating the pH of the water that is used to dilute the formulation prior to application. For instance the surface of silica particles presents silanol groups having a pKa of about 3.5, such that when diluted in water the silanol will be substantially deprotonated at a pH substantially above 3.5, and the silica particles are then susceptible to coulombic repulsion. The integrity of the Pickering emulsion of the water-immiscible dispersed phase may be improved, and the duration may be lengthened for protection of the water-sensitive active ingredient, if the pH is lowered to about 3.5. This may be achieved by the incorporation of an acidifying agent into either the water or the formulated product. Alternatively some colloidal solids have base functionality on their surfaces, in which case their performance may be improved by the addition of an alkali component. Thus one embodiment of the present invention includes the presence of an acidic or a basic component to improve the stabilization effect of respectively the acidic-surface or basic-surface colloidal solid. Suitable acidic or basic components are those that are substantially soluble in any water used to dilute the concentrate formulation prior to application to the target site. Accordingly, in one embodiment such components differ from the colloidal stabilizer described above, even though in some situations the same component could provide either colloidal stabilization or pH-adjustment functionality in different formulations, depending for instance on whether a particular concentrate formulation were to be diluted in water prior to application.

The term "agrochemically active ingredient" refers to chemicals and biological compositions, such as those described herein, which are effective in killing, preventing, or controlling the growth of undesirable pests, such as, plants, insects, mice, microorganism, algae, fungi, bacteria, and the like (such as pesticidally active ingredients). The term may also apply to compounds that control the growth of plants in a desired fashion (e.g., plant growth regulators, ethylene inhibitors), to a compound which mimics the natural systemic activated resistance response found in plant species (e.g., plant activator) or to a compound that reduces the phytotoxic response to a herbicide (e.g., safener). If more than one is present, the agrochemically active ingredients are independently present in an amount that is biologically effective when the composition is diluted, if necessary, in a suitable volume of liquid carrier, e.g., water, and applied to the intended target, e.g., the foliage of a plant or locus thereof.

Water-sensitive agrochemically active ingredients are those subject to a water-mediated degradation such as hydrolysis, oxidation, dehalogenation, bond cleavage, Beckmann rearrangement and other forms of degradation on exposure to water. These materials share the common feature that it is sometimes not feasible to dilute them with water and obtain formulations that display long-term stability.

In one embodiment, the water-sensitive agrochemically active ingredient is solid, but is dissolved in an oily liquid present in the dispersed liquid phase b), is a solid and is dispersed within the dispersed liquid phase or is a solid complex of an agrochemical with a molecular complexing agent and is dispersed within the dispersed liquid phase.

As used herein, the term "degradation" denotes loss of the active ingredient, i.e., the water-sensitive agrochemical, as a result of contact with water. Degradation can be determined simply by measuring the amount of the active ingredient present before and after contact with water.

Examples of water-sensitive agriculturally active ingredients suitable to be entrapped, suspended or dissolved within the dispersed phase b) in accordance with the present invention include, but are not limited to:

the oxyphenoxy acid esters such as clodinafop-propargyl; pinoxaden the sulfonyl ureas such as azimsulfuron, bensulfuron, chlorimuron, chlorsulfuron, cinosulfuron, cyclosulfamuron, ethametsulfuron, ethoxysulfuron, flazasulfuron, flupyrsulfuron, halosulfuron, imazosulfuron, iodosulfuron, mesosulfuron, metsulfuron, nicosulfuron, primisulfuron, prosulfuron, pyrazosulfuron, rimsulfuron, sulfometuron, sulfosulfuron, thifensulfuron, triasulfuron, tribenuron, triflusulfuron, trifloxysulfuron and tritosulfuron;

the cloquintocet herbicide safeners such as cloquintocet-mexyl*;

a PGR that is a solid complex of an agrochemical with a molecular complexing agent such as a cyclopropene molecular encapsulating agent complex, for example, a complex of α-cyclodextrin and 1-MCP. In general, 1-MCP must be protected from water to prevent rapid release of the active ingredient from its molecular cage.

Thiamethoxam (if the aqueous phase is alkaline)

For example, in one method of making a complex in which 1-MCP is encapsulated in a molecular encapsulating agent, the 1-MCP gas is bubbled through a solution of α-cyclodextrin in water, from which the complex first precipitates and is then isolated by filtration. Complexes made by the above method are isolated, dried and stored in solid form, for example as an active ingredient containing powder, for later addition to the inventive dispersion concentrates.

Examples of agrochemical active ingredients suitable for use within the continuous phase a) in accordance with the present invention include, but are not limited to: fungicides such as azoxystrobin, chlorothalonil, cyprodinil, difenoconazole, fludioxonil, mandipropamid, picoxystrobin, propiconazole, pyraclostrobin, tebuconazole, thiabendazole and trifloxystrobin; herbicides such as acetochlor, alachlor, ametryn, anilofos, atrazine, azafenidin, benfluralin, benfuresate, bensulide, benzfendizone, benzofenap, bromobutide, bromofenoxim, bromoxynil, butachlor, butafenacil, butamifos, butralin, butylate, cafenstrole, carbetamide, chloridazon, chlorpropham, chlorthal-dimethyl, chlorthiamid, cinidonethyl, cinmethylin, clomazone, clomeprop, cloransulam-methyl, cyanazine, cycloate, desmedipham, desmetryn, dichlobenil, diflufenican, dimepiperate, dimethachlor, dimethametryn, dimethenamid, dimethenamid-P, dinitramine, dinoterb, diphenamid, dithiopyr, EPTC, esprocarb, ethalfluralin, ethofumesate, etobenzanid, fenoxaprop-ethyl, fenoxaprop-P-ethyl, fentrazamide, flamprop-methyl, flamprop-M-isopropyl, fluazolate, fluchloralin, flufenacet, flumiclorac-pentyl, flumioxazin, fluorochloridone, flupoxam, flurenol, fluridone, flurtamone, fluthiacet-methyl, indanofan, isoxaben, isoxaflutole, lenacil, linuron, mefenacet, mesotrione, metamitron, metazachlor, methabenzthiazuron, methyldymron, metobenzuron, metolachlor, metosulam, metoxuron, metribuzin, molinate, napronilide, napropamide, neburon, norflurazon, orbencarb, oryzalin, oxadiargyl, oxadiazon, oxyfluorfen, pebulate, pendimethalin, pentanochlor, pethoxamid, pentoxazone, phenmedipham, pinoxaden, piperophos, pretilachlor, prodiamine, profluazol, prometon, prometryn, propachlor, propanil, propazine, propham, propisochlor, propyzamide, prosulfocarb, pyraflufen-ethyl, pyrazogyl, pyrazolynate, pyrazoxyfen, pyributicarb, pyridate, pyriminobac-methyl, quinclorac, siduron, simazine, simetryn, S-metolachlor, sulcotrione, sulfentrazone, tebutam, tebuthiuron, terbacil, terbumeton, terbuthylazine, terbutryn, thenylchlor, thiazopyr, thidiazimin, thiobencarb, tiocarbazil, triallate, trietazine, trifluralin, and vernolate; herbicide safeners such as benoxacor, dichlormid, fenchlorazole-ethyl, fenclorim, flurazole, fluxofenim, furilazole, isoxadifen-ethyl, mefenpyr; alkali metal, alkaline earth metal, sulfonium or ammonium cation of mefenpyr; mefenpyr-diethyl and oxabetrinil; insecticides such as abamectin, clothianidin, emamectin benzoate, gamma cyhalothrin, imidacloprid, lambda cyhalothrin, permethrin, resmethrin and thiamethoxam.

One embodiment of the present invention comprises a process for preparing non-aqueous dispersion concentrates as herein described typically by dispersing the water-sensitive a.i. within a suitable water immiscible liquid (oil/solvent) and then mechanically emulsifying such water immiscible liquid comprising the water-sensitive a.i. within a suitable substantially water miscible liquid (solvent) that contains a colloidal solid in order to form the inventive non-aqueous dispersion concentrates.

Further aspects of the invention include a method of preventing or combating infestation of plant species or animals by pests, and regulating plant growth by diluting an amount of concentrate composition with a suitable liquid carrier, such as water or liquid fertilizer, and applying to the plant, tree, animal or locus as desired. The formulations of the present invention may also be combined in a continuous flow apparatus with water in spray application equipment, such that no holding tank is required for the diluted product.

The non-aqueous liquid dispersion concentrate compositions can be stored conveniently in a container from which it is poured, or pumped, or into which a liquid carrier is added prior to application.

The advantages of the non-aqueous liquid dispersion concentrate compositions of the present invention include: storage-stability for extended periods, for example 6 months or longer at room temperature; simple handling is made possible for users because dilution is made with water, or other liquid carrier, for preparation of application mixtures; reduced degradation of water-sensitive active ingredients; negligible change in emulsion droplet size during storage or on dilution; the compositions can easily be resuspended or redispersed with only a minor amount of agitation and/or the emulsions are not susceptible to coalescence when dilution is made with fertilizer solutions for preparation of application mixtures.

The rate of application of the composition of the invention will depend on a number of factors including, for example, the active ingredients chosen for use, the identity of the plants whose growth is to be inhibited and the formulations selected for use and whether the compound is to be applied for foliage or root uptake. As a general guide, however, an application rate of from 1 to 2000 g active ingredient per hectare is suitable, in particular from 2 to 500 g active ingredient per hectare. For 1-MCP and plant growth regulators, use rates are about 0.1 to 50 g per hectare.

In one embodiment, suitable rates for the agrochemically active ingredients used in the inventive compositions are comparable to the existing rates given on the current product labels for products containing such actives. For example, Quadris® brand azoxystrobin can be applied at a rate of from 112 g to 224 g a.i./hectare and Quilt™ brand premix of azoxystrobin (75 g/L)/propiconazole (125 g/L) can be applied at a rate of from 0.75-1.5 L/ha In one embodiment of the present invention, the composition comprises a water-insoluble active ingredient in the form of a solid complex of an agrochemical with a molecular complexing agent and this water-sensitive solid phase is dispersed within a water-immiscible liquid (solvent/oil) that is itself dispersed within a continuous substantially water-miscible liquid phase, thus forming an emulsion of a solid-in-oil, said oil emulsion itself being stabilized by colloidal solids as described above.

In one embodiment of the present invention, a further component may be present to control the pH of the water used to dilute the composition prior to use. In particular if the colloidal solid has acidic groups on the surface, an acidic component may be present, or if the colloidal solid has alkali groups on the surface, an alkali component may be present.

If a water-insoluble solid agrochemically active material is present, the solid active ingredient may be milled to the desired particle size. The solid may be milled in a dry state using an air-mill or other suitable equipment, or it may be milled in the water-immiscible liquid (oil/solvent) with solvent-soluble surfactants as necessary, to achieve the desired particle size. The particle size may be an average particle size of about 0.2 to about 20 microns, suitably about 0.2 to about 15 microns, more suitable about 0.2 to about 10 microns.

As used herein, the term "agrochemically effective amount" means the amount of an agrochemical active compound which adversely controls or modifies target pests or regulates the growth of plants (PGR). For example, in the case of herbicides, a "herbicidally effective amount" is that amount of herbicide sufficient for controlling or modifying plant growth. Controlling or modifying effects include all deviation from natural development, for example, killing, retardation, leaf burn, albinism, dwarfing and the like. The term plants refers to all physical parts of a plant, including seeds, seedlings, saplings, roots, tubers, stems, stalks, foliage and fruits. In the case of fungicides, the term "fungicide" shall mean a material that kills or materially inhibits the growth, proliferation, division, reproduction, or spread of fungi. As used herein, the term "fungicidally effective amount" or "amount effective to control or reduce fungi" in relation to the fungicidal compound is that amount that will kill or materially inhibit the growth, proliferation, division, reproduction, or spread of a significant number of fungi. As used herein, the terms "insecticide", "nematicide" or "acaracide" shall mean a material that kills or materially inhibits the growth, proliferation, reproduction, or spread of insects, nematodes or acarids, respectively. An "effective amount" of the insecticide, nematicide or acaricide is that amount that will kill or materially inhibit the growth, proliferation, reproduction or spread of a significant number of insects, nematodes or acarides.

In one aspect, as used herein, "regulating (plant) growth", "plant growth regulator", PGR, "regulating" or "regulation" includes the following plant responses; inhibition of cell elongation, for example reduction in stem height and internodal distance, strengthening of the stem wall, thus increasing the resistance to lodging; compact growth in ornamentals for the economic production of improved quality plants; promotion of better fruiting; increasing the number of ovaries with a view to stepping up yield; promotion of senescence of the formation of tissue enabling fruit to absciss; defoliation of nursery and ornamental bushes and trees for marl-order business in the fall; defoliation of trees to interrupt parasitic chains of infection; hastening of ripening, with a view to programming the harvest by reducing the harvest to one to two pickings and interrupting the food-chain for injurious insects.

One well-known PGR and ethylene-binding inhibitor is 1-methylcyclopropene (MCP). 1-MCP prevents the signal from ethylene to initiate stress responses in plants and which inhibits the sensitivity of plants or plant parts (e.g. fruits and flowers) to ethylene by inhibiting its perception. Consequently, in another aspect, "regulating (plant) growth", "plant growth regulator", "PGR", "regulating" or "regulation" also includes the use of a composition as defined according to the present invention for increasing the yield and/or improving the vigor of an agricultural plant. According to one embodiment of the present invention, the inventive compositions are used for improved tolerance against stress factors such as fungi, bacteria, viruses and/or insects and stress factors such as heat stress, nutrient stress, cold stress, drought stress, UV stress and/or salt stress of an agricultural plant.

The selection of application rates relative to providing a desired level of pesticidal activity for a composition of the invention is routine for one of ordinary skill in the art. Application rates will depend on factors such as level of pest pressure, plant conditions, weather and growing conditions as well as the activity of the agrochemically active ingredients and any applicable label rate restrictions.

The invention relates also to liquid agrochemical emulsion compositions comprising
  a) a continuous, substantially water-miscible, non-aqueous liquid phase, optionally comprising at least one agrochemically active ingredient, and also optionally comprising at least one acidic or basic component;
  b) a dispersed, water-immiscible, non-aqueous liquid phase comprising at least one substantially water-sensitive agrochemically active ingredient, which is a solid but is dissolved in an oily liquid present in the dispersed phase, is a solid and is dispersed within the dispersed phase or is a solid complex of an agrochemical with a molecular complexing agent and is dispersed within the dispersed phase; and
  c) at least one colloidal solid disposed at the interface between the dispersed phase and the continuous phase.

A further aspect of the invention relates to a dilute aqueous spray composition for combating pests or regulating the growth of plants at a locus comprising
  a) a continuous aqueous phase comprising a suitable liquid carrier, such as water or a liquid fertilizer, in an amount sufficient to obtain the desired final concentration of each of the active ingredients in the spray composition;
  b) a dispersed water-immiscible liquid phase comprising at least one water-sensitive agrochemically active ingredient, which is a solid but is dissolved in an oily liquid present in the dispersed phase, is a solid and is dispersed within the dispersed phase or is a solid complex of an agrochemical with a molecular complexing agent and is dispersed within the dispersed phase;
  c) at least one colloidal solid disposed at the interface between the dispersed phase and the aqueous phase; and
  d) optionally at least one agrochemically active ingredient dispersed, dissolved or emulsified in the aqueous phase; and
  e) optionally at least one acidic or basic component dissolved in the aqueous phase to respectively lower or raise the pH.

In another embodiment, the invention relates to a dilute pesticidal and/or PGR composition for ultra low volume (ULV) application comprising:
  a) a continuous phase comprising a carrier solvent having a flash point above 55° C. in an amount sufficient to obtain the desired final concentration of each of the active ingredients in the ULV composition;
  b) a dispersed water-immiscible liquid phase comprising at least one water-sensitive agrochemically active ingredient, which is a solid but is dissolved in an oily liquid present in the dispersed phase, is a solid and is dispersed within the dispersed phase or is a solid complex of an agrochemical with a molecular complexing agent and is dispersed within the dispersed phase;
  c) at least one colloidal solid disposed at the interface between the dispersed phase and the continuous phase.

The invention relates also to a method for combating or preventing pests in crops of useful plants or regulating the growth of such crops, said method comprising:
  1) treating the desired area, such as plants, the plant parts or the locus thereof with a concentrate composition comprising:
     a) a continuous substantially water-miscible, non-aqueous liquid phase, optionally comprising at least one agrochemically active ingredient, and also optionally comprising at least one acidic or basic component;
     b) a dispersed water-immiscible liquid phase comprising at least one water-sensitive agrochemically active ingredient, which is a solid but is dissolved in an oily liquid present in the dispersed phase, is a solid and is dispersed within the dispersed phase or is a solid complex of an agrochemical with a molecular complexing agent and is dispersed within the dispersed phase; and
     c) at least one colloidal solid disposed at the interface between the dispersed phase and the continuous phase; or
  2) diluting the concentrate composition, if necessary, in a suitable carrier, such as water, liquid fertilizer or a carrier solvent having a flash point above 55° C., in an amount sufficient to obtain the desired final concentration of each of the active ingredients (a.i.); and then treating the desired area, such as plants, the plant parts or the locus thereof with the dilute spray or ULV composition.

The term plants refers to all physical parts of a plant, including seeds, seedlings, saplings, roots, tubers, stems, stalks, foliage and fruits. The term locus refers to where the plant is growing or is expected to grow.

The composition according to the invention is suitable for all methods of application conventionally used in agriculture, e.g. pre-emergence application, post-emergence application and seed dressing. The compositions according to the invention are suitable for pre- or post-emergence applications to crop areas.

The compositions according to the invention are suitable especially for combating and/or preventing pests in crops of useful plants or for regulating the growth of such plants. Preferred crops of useful plants include canola, cereals such as barley, oats, rye and wheat, cotton, maize, soya, sugar beets, fruits, berries, nuts, vegetables, flowers, trees, shrubs and turf. The components used in the composition of the invention can be applied in a variety of ways known to those skilled in the art, at various concentrations. The rate at which the compositions are applied will depend upon the particular type of pests to be controlled, the degree of control required, and the timing and method of application.

Crops are to be understood as also including those crops which have been rendered tolerant to herbicides or classes of herbicides (e.g. ALS-, GS-, EPSPS-, PPO-, ACCase and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTN33B® (cotton), Bollgard® (cotton), NewLeaf® (potatoes), Nature-Gard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

Crop areas are areas of land on which the cultivated plants are already growing or in which the seeds of those cultivated plants have been sown, and also areas of land on which it is intended to grow those cultivated plants.

Other active ingredients such as herbicide, plant growth regulator, algaecide, fungicide, bactericide, viricide, insecticide, acaricide, nematicide or molluscicide may be present in the emulsion formulations of the present invention or may be added as a tank-mix partner with the emulsion formulations.

The compositions of the invention may further comprise other inert additives. Such additives include thickeners, flow enhancers, wetting agents, antifoaming agents, biocides, lubricants, fillers, drift control agents, deposition enhancers, adjuvants, evaporation retardants, freeze protecting agents, insect attracting odor agents, UV protecting agents, fragrances, and the like. The thickener may be a compound that is soluble or able to swell in water, such as, for example, polysaccharides of xanthans (e.g., anionic heteropolysaccharides such as RHODOPOL® 23 (Xanthan Gum)(Rhodia, Cranbury, N.J.)), alginates, guars or celluloses; synthetic macromolecules, such as polyethylene glycols, polyvinyl pyrrolidones, polyvinyl alcohols, modified cellulose-based polymers, polycarboxylates, bentonites, montmorillonites, hectonites, or attapulgites. The freeze protecting agent may be, for example, ethylene glycol, propylene glycol, glycerol, diethylene glycol, saccharose, water-soluble salts such as sodium chloride, sorbitol, triethylene glycol, tetraethylene glycol, urea, or mixtures thereof. Representative anti-foam agents are polydialkylsiloxanes, in particular polydimethylsiloxanes, fluoroaliphatic esters or perfluoroalkylphosphonic/perfluoroalkylphosphonic acids or the salts thereof and mixtures thereof. Preferred are polydimethylsiloxanes, such as Dow Corning® Antifoam A or Antifoam B. Representative biocides include 1,2-benzisothiazolin-3-one, available as PROXEL® GXL (Arch Chemicals).

The compositions of the invention may be mixed with fertilizers and still maintain their stability. For example, when the compositions of the invention are mixed with fertilizers, they do not exhibit any irreversible flocculation after about one hour and they show no tendency to coalescence. The fertilizers may comprise, for example, sulfur, nitrogen, phosphorous, and/or potassium.

The compositions of the invention may be used in conventional agricultural methods. For example, the compositions of the invention may be mixed with water and/or fertilizers and may be applied preemergence and/or postemergence to a desired locus by any means, such as airplane spray tanks, direct injection spray equipment, knapsack spray tanks, cattle dipping vats, farm equipment used in ground spraying (e.g., boom sprayers, hand sprayers), and the like. The desired locus may be soil, plants, and the like.

The dispersion concentrates of the present invention typically are prepared by dispersing the water-sensitive a.i. within a suitable water-immiscible liquid and then the liquid comprising the water-sensitive a.i. is emulsified within a suitable substantially water-miscible liquid to form the concentrate utilizing a colloidal solid as the emulsifying agent.

In one embodiment, the dispersion concentrate is prepared by first adding the water-sensitive agrochemical to the water-immiscible liquid (oil/solvent) along with an optional water-insoluble polymer as dispersing aid and stirring until the a.i. is fully dispersed/suspended therein. Second, a colloidal solid is added to the continuous substantially water-miscible liquid (solvent) and the resulting mixture is stirred under high shear using a suitable mixer until the colloidal solid is fully dispersed/homogenous. Next, the water-immiscible liquid—a.i. mixture is then dispersed within the substantially water-miscible liquid phase under high shear conditions using a suitable mixer until the dispersed oil droplet particle size is between about 20 to about 100 microns in diameter. At least one optional emulsifier and viscosity modifying agent is then added to the concentrate. Suitable viscosity modifying agents include nonionic surfactants with high HLB, most particularly with an HLB above about 12, which substantially reduces the high-shear viscosity of the concentrate such it has desirable handling properties.

In some embodiments, one or more metal complexing or chelating agents such as EDTA may also be present in the dispersed or continuous phases if necessary to protect the agrochemical from degradation mediated by metal ions present in the water or other liquid used to dilute the concentrate prior to use.

In some embodiments, the dispersion concentrate of the present invention does not include one or more metal-complexing or chelating agents.

In some embodiments a water-soluble acidic or basic component may also be present in the dispersed or continuous phases to respectively lower or raise the pH of water used to dilute the dispersion concentrate prior to use.

The following examples illustrate further some of the aspects of the invention but are not intended to limit its scope. Where not otherwise specified throughout this specification and claims, percentages are by weight.

Example 1

The dispersed phase was prepared as follows: 3.4 g of Agrimer AL22 (ISP) was dissolved by stirring in 38.6 g of Isopar V (Exxon-Mobil), to which was added 58 g of α-cyclodextrin/MCP complex that had been air-milled to median particle diameter below 10 micron. The continuous phase was prepared as follows: 4.8 g of Aerosil R974 (Evonik) was dispersed in 136.7 g of propylene carbonate under high shear using a Turrax rotor-stator mixer. While applying continuous high shear with a Cowles blade turbine, 96 g of the dispersed phase was added to create a colloid-stabilized emulsion of the dispersed phase in the propylene carbonate continuous phase. With continuous low shear to achieve homogeneity, to this emulsion was added 3.4 g of Agrimer VA5I (ISP). The dispersion concentrate was examined by microscope under polarized light filter to visualize the crystals of agrochemicals and it was verified that substantially all of the agrochemical crystals had been retained within the dispersed phase. The storage modulus of the dispersion concentrate was determined to be 80 Pa at a strain amplitude below 0.01% under oscillatory shear at 1 Hz, indicating a moderately viscous fluid dispersion.

Example 2

To the 76.7 g of the dispersion concentrate from example 1 was added 1.6 g of Atlox MBA 13/30 (Croda), 0.16 g Tween 21 (Croda) and 0.24 g Soprophor 3D33 (Rhodia). The resulting concentrate had excellent flowability and formed a fine dispersion when diluted into water. The storage modulus of the dispersion concentrate was determined to be 2.1 Pa at a strain amplitude below 0.01% under oscillatory shear at 1 Hz, and 0.4 Pa at a strain amplitude of 100% under oscillatory shear at 1 Hz, consistent with a fluid dispersion of good handling properties.

Example 3

A concentrated formulation was prepared identically to that in example 2, except that the Atlox MBA 13/30 was replaced with 1.6 g of Tetronic 1107 (BASF). The resulting concentrate had excellent flowability and formed a fine dispersion when diluted into water.

Example 4

A concentrated formulation was prepared identically to that in example 2, except that the Atlox MBA 13/30 was replaced with 1.6 g of Toximul 8320 (Stepan). The resulting concentrate had excellent flowability and formed a fine dispersion when diluted into water. The storage modulus of the dispersion concentrate was determined to be 6.7 Pa at a strain amplitude below 0.01% under oscillatory shear at 1 Hz, and below 1 Pa at a strain amplitude of 100% under oscillatory shear at 1 Hz, consistent with a fluid dispersion of good handling properties.

Example 5

Approximately 3 mg of α-cyclodextrin/MCP complex powder was added to 3 mL of a solution of 0.4 wt % Kinetic surfactant (Helena) in water in a 122 mL glass vial and the vial was sealed with a rubber septum. While the powder suspension was stirred with a magnetic stir bar at 80 rpm, the release of 1-MCP into the headspace was monitored by gas chromatography analysis of aliquots of the headspace gas. After 10 minutes of stirring, 91% of the 1-MCP present had been released.

Example 6

The dispersed phase was prepared as follows: 2.5 g of Agrimer AL22 (ISP) was dissolved by stirring in 45.1 g of Isopar V (Exxon-Mobil), to which was added 54.9 g of α-cyclodextrin/MCP complex that had been air-milled to median particle diameter below 10 micron. The continuous phase was prepared as follows: 3.9 g of Aerosil R974 (Evonik) was dispersed in 162.4 g of propylene carbonate under high shear using a Turrax rotor-stator mixer. While applying continuous high shear with a Cowles blade turbine, 77.5 g of the dispersed phase was added to create a colloid-stabilized emulsion of the dispersed phase in the propylene carbonate continuous phase. With continuous low shear to achieve homogeneity, to this emulsion was added 3.75 g of Agrimer VA5I (ISP), then 2.5 g of Rhodasurf BC-610, and then 1.0 g of EDTA tetrasodium salt as a fine powder. The resulting dispersion concentrate had a median particle size when dispersed in water of 90 microns. The release of 1-MCP into headspace was monitored as in example 5. After 15 minutes of stirring, 52% of the 1-MCP present had been released, confirming that the dispersion concentrate substantially inhibited release of the agrochemical under aggressive stirring conditions in water.

Example 7

The dispersed phase was prepared as follows: 3.75 g of Agrimer AL22 (ISP) was dissolved by stirring in 82.5 g of Isopar V (Exxon-Mobil), to which was added 82.5 g of α-cyclodextrin/MCP complex that had been air-milled to median particle diameter below 10 micron. The continuous phase was prepared as follows: 1.4 g of Aerosil R974 (Evonik) was dispersed in 82.5 g of ethyl lactate under high shear using a Turrax rotor-stator mixer. While applying continuous high shear with a Cowles blade turbine, 27.5 g of the dispersed phase was added to create a colloid-stabilized emulsion of the dispersed phase in the ethyl lactate continuous phase. With continuous low shear to achieve homogeneity, to this emulsion was added 1.65 g of Agrimer VA5I (ISP) and 0.28 g of EDTA as a fine powder, then 1.1 g of Rhodasurf BC-610. The resulting dispersion concentrate formed a fine dispersion on dilution in water with a median particle diameter of 28 microns.

Example 8

The dispersion concentrate was prepared as in example 7 except that the ethyl lactate was replaced by triacetin. The resulting dispersion concentrate formed a fine dispersion on dilution in water with a median particle diameter of 121 microns.

Example 9

The dispersion concentrate was prepared as in example 7 except that the ethyl lactate was replaced by di(propylene glycol) methyl ether acetate. The resulting dispersion concentrate formed a fine dispersion on dilution in water with a median particle diameter of 95 microns.

Example 10

The dispersed phase was prepared as follows: 2.5 g of Agrimer AL22 (ISP) was dissolved by stirring in 69.6 g of Isopar V (Exxon-Mobil), to which was added 16 g of primilsulfuron that had been air-milled to median particle diameter below 10 micron, 16 g of atrazine that had been air-milled to median particle diameter below 10 micron and 16 g of trifloxysulfuron that had been air-milled to median particle diameter below 10 micron. The continuous phase was prepared as follows: 5.25 g of Aerosil R974 (Evonik) was dispersed in 189.8 g of propylene carbonate under high shear using a Turrax rotor-stator mixer. 105 g of the dispersed phase was added to the continuous phase and high shear was applied with a Cowles blade turbine to create a colloid-stabilized emulsion of the dispersed phase in the propylene carbonate continuous phase. The dispersion concentrate was examined by microscope under polarized light filter to visualize the crystals of agrochemicals and it was verified that substantially all of the crystals had been retained within the dispersed phase.

Example 11

The dispersed phase was prepared as follows: 2.75 g of Agrimer AL22 (ISP) was dissolved by stirring in 42.25 g of Isopar V (Exxon-Mobil), to which was added 55 g of α-cyclodextrin/MCP complex that had been air-milled to median particle diameter below 10 micron. The continuous phase was prepared as follows: 2.5 g of Aerosil R974 (Evonik) was dispersed in 121.5 g of propylene carbonate under high shear using a Turrax rotor-stator mixer. While applying continuous high shear with a Cowles blade turbine, 70 g of the dispersed phase was added to create a colloid-stabilized emulsion of the dispersed phase in the propylene carbonate continuous phase. With continuous low shear to achieve homogeneity, to this emulsion was added 3 g of Agrimer VA5I (ISP), then 2 g of Toximul 8320. The dispersion concentrate was then divided into two sub-samples. To one sub-sample 0.5 wt % of EDTA acid was added and the other was left as a control. The release of 1-MCP into headspace from both sub-samples was monitored as in example 5, except that the stirrer speed was increased to 160 rpm. After 80 minutes of stirring, 85% of the 1-MCP present had been released from the control sub-sample, whereas the for the sub-sample with 0.5 wt % of EDTA acid added, only 63% of the 1-MCP present had been released. This confirms that the EDTA acid inhibited release of 1-MCP from the dispersion concentrate under aggressive stirring conditions in water.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

We claim:

1. A physically stable, non-aqueous liquid dispersion concentrate composition comprising
   (a) a continuous substantially water-miscible, non-aqueous liquid phase comprising a non-aqueous liquid that forms a single phase when present in water at a concentration up to at least 50 wt %;
   (b) a dispersed water-immiscible, non-aqueous liquid phase comprising droplets of a water-immiscible liquid with a log P above 3 having a volume-weighted median diameter as measured by diffraction light scattering of about 200 microns or less, which droplets contain at least one water-sensitive agrochemically active ingredient dispersed or dissolved therein; and
   (c) a colloidal solid disposed at the interface between the dispersed phase and the continuous phase.

2. The composition of claim 1 wherein the dispersed phase (b) comprises at least one water-sensitive agrochemically active ingredient selected from the group consisting of: a solid dissolved in the dispersed phase (b), a solid dispersed within (b), and a solid complex of an agrochemical with a molecular complexing agent dispersed within (b).

3. The composition of claim 2, wherein the water-sensitive agrochemically active ingredient comprises a solid complex of an alkyl-cyclopropene and a molecular encapsulating agent.

4. The composition of claim 3, wherein the complex of an alkyl-cyclopropene and a molecular encapsulating agent is a complex of 1 methylcyclopropene and -alpha-cyclodextrin.

5. The composition of claim 2, wherein the water-sensitive agrochemically active ingredient is a compound selected from thiamethoxam, oxyphenoxy acid esters, sulfonyl ureas and cloquintocet herbicide safeners.

6. The composition of claim 1, wherein the (a) comprises at least one agrochemically active ingredient.

7. The composition of claim 6, wherein the agrochemically active ingredient present in the continuous phase comprises a strobilurin fungicide.

8. The composition of claim 7, wherein the strobilurin fungicide comprises azoxystrobin.

9. The composition of claim 6, wherein the agrochemically active ingredient present in the continuous phase comprises an azole fungicide.

10. The composition of claim 9, wherein the azole fungicide comprises propiconazole.

11. The composition of claim 1, wherein the water-immiscible liquid is selected from petroleum distillates, vegetable oils, silicone oils, methylated vegetable oils, alkyl-amides, alkyl-acetates, refined paraffins, isoparaffinic hydrocarbons, mineral oils, and mixtures thereof.

12. The composition of claim 11, wherein the water-immiscible liquid is selected from isoparaffinic hydrocarbons.

13. The composition of claim 1, wherein (a) comprises a substantially water-miscible, non-aqueous liquid that forms a single phase when present in water at a concentration up to 50 wt %.

14. The composition of claim 13, wherein (a) comprises a substantially water-miscible, non-aqueous liquid that is fully miscible with water in all proportions.

15. The composition of claim 1, wherein (a) comprises propylene carbonate.

16. The composition of claim 1, further comprising at least one water-insoluble polymer that is soluble or miscible in the dispersed phase (b).

17. The composition of claim 1, wherein the composition further comprises at least one emulsifier or viscosity modifier in the continuous phase (a).

18. The composition of claim 17, wherein the composition comprises at least one viscosity modifying agent that is a nonionic surfactant having an HLB above about 12 in the continuous phase (a).

19. The composition of claim 1, which comprises at least one metal complexing or chelating agent.

20. The composition of claim 17, comprising a chelating agent selected from EDTA.

21. The composition of claim 1, which comprises at least one water-soluble acidic component, in an amount sufficient to lower the pH of water by at least about 1 unit when the composition is diluted into that water.

22. The composition of claim 1, which comprises at least one water-soluble basic component, in an amount sufficient to raise the pH of water by at least about 1 unit when the composition is diluted into that water.

* * * * *